US007652773B2

(12) United States Patent
DiMarzio et al.

(10) Patent No.: US 7,652,773 B2
(45) Date of Patent: Jan. 26, 2010

(54) ENHANCED DETECTION OF ACOUSTO-PHOTONIC EMISSIONS IN OPTICALLY TURBID MEDIA USING A PHOTO-REFRACTIVE CRYSTAL-BASED DETECTION SYSTEM

(75) Inventors: Charles A. DiMarzio, Cambridge, MA (US); Ronald A. Roy, Mansfield, MA (US); Todd W. Murray, Medford, MA (US); Florian J. Blonigen, Jamaica Plain, MA (US); Luis A. Nieva, Roslindale, MA (US); Lei Sui, Brighton, MA (US); Gopi Maguluri, Allston, MA (US)

(73) Assignees: Northeastern University, Boston, MA (US); Trustees of Boston University, Boston, MA (US)

( * ) Notice: Subject to any disclaimer, the term of this patent is extended or adjusted under 35 U.S.C. 154(b) by 150 days.

(21) Appl. No.: 10/586,713

(22) PCT Filed: Jan. 20, 2005

(86) PCT No.: PCT/US2005/002226

§ 371 (c)(1),
(2), (4) Date: Nov. 20, 2007

(87) PCT Pub. No.: WO2005/069997

PCT Pub. Date: Aug. 4, 2005

(65) Prior Publication Data

US 2008/0094633 A1 Apr. 24, 2008

Related U.S. Application Data

(60) Provisional application No. 60/537,792, filed on Jan. 20, 2004.

(51) Int. Cl.
*G01B 9/02* (2006.01)

(52) U.S. Cl. ........................................ 356/502

(58) Field of Classification Search ................ 356/450, 356/497, 502
See application file for complete search history.

(56) References Cited

U.S. PATENT DOCUMENTS

| | | | | |
|---|---|---|---|---|
| 5,131,748 A * | 7/1992 | Monchalin et al. | .......... | 356/486 |
| 5,174,298 A | 12/1992 | Dolfi et al. | .................. | 128/665 |
| 5,951,481 A | 9/1999 | Evans | ......................... | 600/473 |
| 6,041,248 A | 3/2000 | Wang | ......................... | 600/407 |
| 6,115,127 A * | 9/2000 | Brodeur et al. | ............. | 356/503 |

* cited by examiner

*Primary Examiner*—Hwa S Lee (Andrew)
(74) *Attorney, Agent, or Firm*—Weingarten, Schurgin, Gagnebin & Lebovici LLP

(57) ABSTRACT

A system and method of detecting acousto-photonic emissions in optically turbid media that provide increased levels of detection sensitivity. The detection system includes an ultrasonic transducer, a laser, a photo-detector for detecting ultrasound-modulated laser light, and circuitry for processing the detected signals for subsequent analysis. The ultrasonic transducer generates an ultrasonic wave that propagates within an optically turbid medium. The laser generates a coherent light beam, which is split to form signal and reference beams. The signal beam is sent through the turbid medium, where it is phase modulated by the ultrasound. The ultrasound-modulated signal beam is provided to a photo-refractive crystal for subsequent interference with the reference beam to convert the phase modulation to intensity modulation. The DC offset of the signal beam intensity provides a measure of the magnitude of the mean phase shift induced by the ultrasound on the multiply scattered optical field within the turbid medium.

12 Claims, 5 Drawing Sheets

ENHANCED DETECTION OF ACOUSTO-PHOTONIC EMISSIONS IN OPTICALLY TURBID MEDIA USING A PHOTO-REFRACTIVE CRYSTAL-BASED DETECTION SYSTEM

CROSS REFERENCE TO RELATED APPLICATIONS

This application claims priority of U.S. Provisional Patent Application No. 60/537,792 filed Jan. 20, 2004 entitled ENHANCED DETECTION OF ACOUSTO-PHOTONIC EMISSIONS IN OPTICALLY TURBID MEDIA USING A PHOTO-REFRACTIVE CRYSTAL-BASED DETECTION SYSTEM.

STATEMENT REGARDING FEDERALLY SPONSORED RESEARCH OR DEVELOPMENT

This invention was made with government support under U.S. Government Contract No. EEC-9986821 awarded by the Center for Subsurface Sensing and Imaging Systems (CenSSIS) under the Engineering Research Centers Program of the National Science Foundation. The government has certain rights in the invention.

BACKGROUND OF THE INVENTION

The present invention relates generally to optical tomography, and more specifically to a system and method of detecting acousto-photonic emissions in optically turbid media.

In recent years, optical imaging techniques have been increasingly employed in the field of biomedical imaging. Optical imaging yields important advantages in the biomedical imaging field due to its ability to locate objects and/or abnormalities in biological tissue without requiring the use of ionizing radiation. For example, optical imaging techniques have been used to detect breast cancer, to perform functional imaging of the brain and for stroke differentiation, to determine the health of fetuses, and to perform mechanical and optical tissue characterizations. Because the optical properties of diseased biological tissue typically vary from that of healthy tissue, optical imaging techniques can detect tissue abnormalities such as breast cancer based on the optical differences of the diseased and healthy tissue. Such use of optical imaging has drawbacks, however, because biological tissue is a turbid medium, and laser light typically used in optical imaging techniques generally undergoes a high degree of scattering within turbid media. As a result, good spatial resolution using optical imaging techniques in biomedical imaging has been difficult to achieve.

More recently, optical imaging has been employed in conjunction with ultrasonic techniques to improve spatial resolution in biomedical imaging. Whereas laser light is generally highly scattered within biological tissue, ultrasonic waves generally scatter much less readily within such tissue and can therefore provide good spatial resolution even at depth. Biomedical imaging using a combination of optical imaging and ultrasonic techniques is known by various names including acousto-photonic imaging, ultrasound tagging of light, acousto-optic tomography, acousto-optic imaging, and ultrasound-modulated optical tomography.

For example, in a typical mode of operation, an ultrasonic wave is propagated within a turbid medium of biological tissue, and laser light is sent through the tissue where it is modulated by the ultrasonic wave. There are three primary mechanisms for ultrasonic modulation of the laser light. In a first mechanism, the ultrasonic wave generates a pressure variation in the medium of interest to induce a density change in the medium. The optical absorption, the scattering coefficient, and the index of refraction of the medium vary with the change in density, and the light is modulated in response to these parameter changes. In a second mechanism, the ultrasonic wave generates particle displacement within the medium, thereby causing optical path lengths to change. These optical path length changes cause speckles to form, which subsequently lead to changes in the intensity of the light. In a third mechanism, the ultrasonic wave acts like a phonon, and the phonons interact with the photons from the laser, causing a Doppler shift of the optical frequency by the ultrasonic frequency. The optical detector operates as a heterodyning device between the Doppler shifted light and the non-shifted light to produce a signal of the ultrasonic frequency.

Next, the ultrasound-modulated light emitted from the tissue is detected, and the detected signal is analyzed to determine the location(s) of abnormalities within the tissue. Because the interaction region of the ultrasonic wave and the laser light is generally defined by the dimensions of the ultrasonic beam and/or the size of the acoustic focal region, and because the signals detected at the frequency of the ultrasonic wave correspond only to the light that has passed through the ultrasonic beam, spatial resolution in biomedical imaging can be significantly increased.

Various methods have been employed to detect emissions of ultrasound-modulated laser light in acousto-photonic imaging. For example, ultrasound-modulated laser light may be detected using a single high-speed detector such as a photo-multiplier tube (PMT) detector or an avalanche photodiode (APD) detector. According to one detection method using a single detector, the mutual interference of partially coherent laser light produces a speckle pattern, and the single detector may have a detection aperture operative to receive either a single speckle or multiple speckles for subsequent analysis. The single speckle detection method, however, operates on very low levels of light, and therefore typically provides a low signal-to-noise ratio (SNR). Further, the multiple speckle detection method typically results in a reduced modulation depth.

Ultrasound-modulated laser light may also be detected using a charge-coupled device (CCD) array. According to one detection method using a CCD array, the size of a speckle is adjusted for approximately matching the size of a single pixel of the CCD array. Next, the modulation amplitude at each pixel is measured, and the measured modulation amplitudes are summed. Such a detection method typically results in an increased SNR. The ultrasound-modulated laser light may also be detected by measuring changes in the modulation depth on the CCD array.

Each one of the above-described methods of detecting emissions of ultrasound-modulated laser light has drawbacks, however, because the signals detected by such methods are typically very weak. As a result, the sensitivity of these detection methods, particularly in biomedical imaging, is typically very low. Although spatial integration may theoretically be employed to provide a stronger signal for increased sensitivity, the randomness introduced by speckle patterns generally reduces the effectiveness of spatial integration. Temporal integration may also be ineffective at increasing sensitivity if the biological tissue of interest undergoes any movement during the acousto-photonic imaging process.

It would therefore be desirable to have an improved system and method of detecting acousto-photonic emissions in optically turbid media such as biological tissue. Such an improved system and method would provide increased detection sensitivity, while avoiding the drawbacks of the above-described conventional acousto-photonic emission detection techniques.

BRIEF SUMMARY OF THE INVENTION

In accordance with the present invention, a system and method of detecting acousto-photonic emissions in optically turbid media are disclosed that provide increased levels of detection sensitivity. In one embodiment, the detection system comprises a sound source including an ultrasonic transducer, an optical signal source including a laser, a photodetector for detecting ultrasound-modulated laser light, and circuitry for processing the detected signals for subsequent analysis. In the preferred embodiment, the ultrasound-modulated light detector includes a photo-refractive crystal (PRC).

In one mode of operation, the ultrasonic transducer generates an ultrasonic wave that propagates within an optically turbid medium such as biological tissue. Further, the laser generates a coherent beam of light, which is split to form a signal beam and a reference beam. The signal beam is sent through the turbid medium, where it is phase modulated in the presence of the ultrasound. Next, the ultrasound-modulated signal beam is emitted from the turbid medium and provided to the photo-refractive crystal, which mixes the signal beam with the reference beam to form an interference pattern. Specifically, the index of refraction of the photo-refractive crystal is modulated through the electro-optic effect, and the reference beam is diffracted off of the index grating into the direction of the signal beam in a two-wave mixing process. The diffracted reference beam and the emitted signal beam interfere with one another to cause the phase modulation encoded on the signal beam to be converted to intensity (i.e., amplitude) modulation.

In the presently disclosed embodiment, the photo-refractive crystal is adaptive such that the index grating is conceptually continually re-written on the time scale of the PRC response time. As a result, a relative phase shift is produced between the signal beam and the reference beam, thereby causing a change in intensity to be detected at the photodetector. The intensity of the signal beam has an AC component and a DC offset having an amplitude that is a function of the modulated photon density and thus the attenuation coefficient of the turbid medium in the light/sound interaction region. This allows the imaging of regions with different absorption coefficients, even if the modulation depth (for a given photon flux) is the same. Because the DC offset is a function of the modulated photon density, the DC offset can be used as a measure of the magnitude of the mean phase shift induced by the ultrasound on the multiply scattered optical field within the turbid medium. In addition, changes in the magnitude of the mean phase shift may be indicative of an object or an abnormality at the interaction region of the ultrasonic wave and the laser light within the turbid medium. Because the DC offset is typically significantly larger than the AC component of the signal beam, the DC offset signal can be used to detect objects or abnormalities within a turbid medium with increased levels of sensitivity.

It should be noted that the output generated by the PRC detector possesses an AC component at the ultrasound frequency, and a DC component that is a function of the incident light illumination level and the acousto-photonic modulation depth. Significant changes to any of these physical parameters caused by changes in the properties of the turbid medium are sensed by the system with a spatial resolution that depends primarily on the spatial pulse length and the lateral shape of the ultrasound beam.

It is further noted that when using short ultrasound pulses and processing signals in the time domain, the spatial resolution of the measurement is determined (along the acoustic axis) by the spatial length of the acoustic pulse and (off-axis) by the diameter of the beam. When using CW ultrasound, the spatial resolution is determined (along the acoustic axis) by the non-linearity of the acousto-photonic interaction and (off-axis) by the diameter of the beam.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which.

DETAILED DESCRIPTION OF THE INVENTION

U.S. Provisional Patent Application No. 60/537,792 filed Jan. 20, 2004 entitled ENHANCED DETECTION OF ACOUSTO-PHOTONIC EMISSIONS IN OPTICALLY TURBID MEDIA USING A PHOTO-REFRACTIVE CRYSTAL-BASED DETECTION SYSTEM is incorporated herein by reference.

A system and method of detecting acousto-photonic emissions in optically turbid media is disclosed that provides increased levels of detection sensitivity. The presently disclosed detection system is based on a photo-refractive crystal (PRC), which receives a reference light beam and a signal light beam corresponding to the acousto-photonic emission. The photo-refractive crystal implements a two-wave mixing process for converting optical phase modulation encoded on the signal beam to intensity (i.e., amplitude) modulation. The intensity of the signal beam has an AC component, and a DC offset having an amplitude that is a function of the modulated photon density and thus the attenuation coefficient of the turbid medium in the light/sound interaction region. The DC offset of the signal beam intensity can be used to detect objects or abnormalities within turbid media with increased levels of sensitivity.

Figure 1:
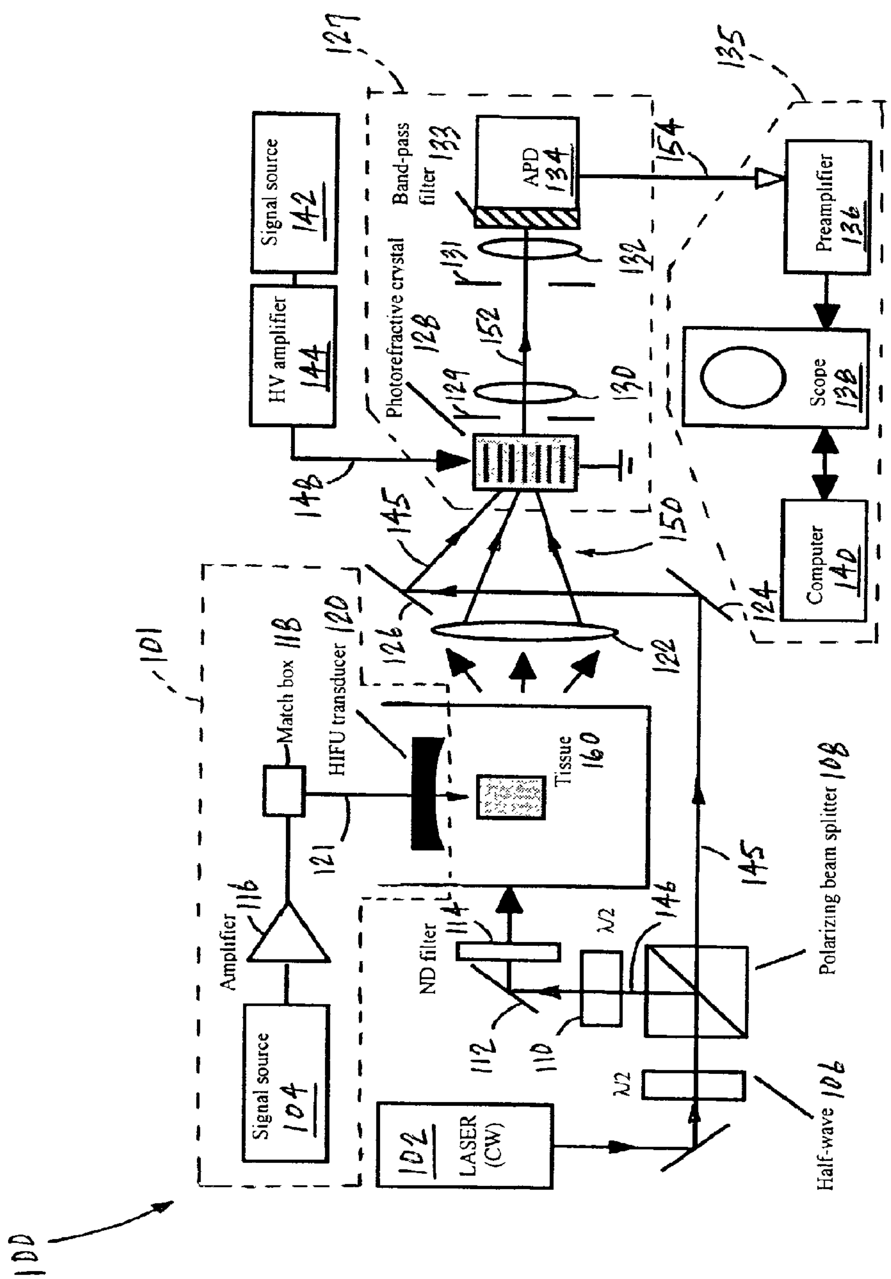
FIG. 1 is a block diagram of a system for detecting acousto-photonic emissions in optically turbid media according to the present invention.

FIG. 1 depicts an illustrative embodiment of a system 100 for detecting acousto-photonic emissions in optically turbid media, in accordance with the present invention. In the illustrated embodiment, the detection system 100 comprises a sound source 101, an optical signal source 102 such as a laser, a photo-detector 127, and signal processing and analysis units 135. Specifically, the sound source 101 includes a first signal source 104, an amplifier 116, an impedance matching unit 118, and a high frequency ultrasonic transducer 120. Moreover, the photo-detector 127 includes a photo-refractive crystal (PRC) 128, a pair of apertures 129 and 131, lenses 130 and 132, a laser line band-pass filter 133, and a photo-diode 134 such as an avalanche photo-diode (APD) In addition, the signal processing/analysis units 135 include a preamplifier 136, an oscilloscope 138, and a computer 140.

The detection system 100 further includes a half-wave plate 106 and a polarizing beam-splitter 108 for producing a reference light beam 145 and a signal light beam 146, a half-wave plate 110, a neutral density (ND) filter 114, a lens 122, mirrors 124 and 126, a second signal source 142, and a high voltage (HV) amplifier 144. The signal source 142 and the HV amplifier 144 are operative for optionally applying an AC field to the photo-refractive crystal 128, as described in greater detail below.

In the presently disclosed embodiment, the detection system 100 is configured to perform acousto-photonic imaging for detecting objects or abnormalities within a turbid medium such as a biological tissue sample 160. Those of ordinary skill in this art will appreciate that acousto-photonic imaging is a two-wave mixing process, in which a diffusive photon wave in a turbid medium interacts with an imposed acoustic field that drives scattered photons within the medium to coherent periodic motion. As a result, a phase-modulated photon field is emitted from the interaction region of the photon wave and the acoustic field within the turbid medium, carrying information relating to the local opto-mechanical properties of the medium.

According to the present invention, the photo-refractive crystal 128 is employed for mixing a diffusely scattered signal beam 150 emanating from the biological tissue 160 with the reference beam 145. The diffuse signal beam 150 interferes with the reference beam 145 in the two-wave mixing process to cause the phase modulation encoded on the signal beam 150 to be converted to intensity (i.e., amplitude) modulation. As described in greater detail below, the intensity of the signal beam 150 has an AC component, and a DC offset having an amplitude that is a function of the modulated photon density and thus the attenuation coefficient of the turbid medium in the light/sound interaction region. This DC offset of the signal beam intensity can be used to detect objects or abnormalities within the tissue 160 with a high level of sensitivity.

In the preferred mode of operating the detection system 100 (see FIG. 1), the sound source 101 generates a pulse train for driving the ultrasonic transducer 120. For example, the sound source 101 may generate a pulse train comprising 20 cycle pulses with a pulse repetition frequency (PRF) of 100 Hz, or any other suitable pulse train. Specifically, the signal source 104 operates as a function generator for producing the pulse train, and provides the pulse train to the amplifier 116, which is a fixed gain power amplifier. Next, the amplifier 116 provides the amplified drive signal to the impedance matching unit 118, which in turn provides the drive signal to the ultrasonic transducer 120. The ultrasonic transducer 120 then produces an ultrasonic signal 121 directed toward the biological tissue 160.

For example, the ultrasonic transducer 120 may comprise a single-element, spherically focused, piezoelectric transducer, or any other suitable acoustic transducer. Moreover, in the presently disclosed embodiment, the biological tissue 160 is disposed in a tank of degassed, filtered, de-ionized water. The ultrasonic transducer 120 has a focal distance of about 6.32 cm (measured in the degassed water at 28° C.) and an aperture of about 7.0 cm. The center frequency of the transducer 120 is about 1.1 MHz, and the bandwidth ranges from about 0.85 MHz to 1.35 MHz. The focal region, as defined by the full width of half maximum intensity (FWHM), is a substantially cigar-shaped ellipsoid with a long axis of about 9 mm and a short axis of about 1.5 mm. It should be understood, however, that the ultrasonic transducer 120 may alternatively comprise any other suitable single-element acoustic transducer, or any suitable acoustic transducer array. It should also be appreciated that the biological tissue 160 is disposed in the tank of water for purposes of illustration only, and that any other suitable arrangement for positioning a turbid medium of interest may be employed.

In the preferred mode of operation, the laser 102 provides a linearly polarized Gaussian light beam to the beam-splitter 108 via the half-wave plate 106. As shown in FIG. 1, the beam-splitter 108 splits the beam provided by the laser 102 into the reference beam 145 and the signal beam 146. The beam-splitter 108 directs the reference beam 145 toward the mirror 124, which in turn directs the beam toward the mirror 126, thereby providing the reference beam 145 directly to the photo-refractive crystal 128. In addition, the beam-splitter 108 directs the signal beam 146 toward the mirror 112 via the half-wave plate 110. Next, the mirror 112 directs the signal beam 146 toward the biological tissue 160 via the ND filter 114, which may be employed to adjust the power of the signal beam. It is noted that the signal beam 146 is directed toward the tissue 160 at about a 90° angle to the direction of the ultrasonic signal 121. The diffusely-scattered ultrasound-modulated signal beam 150 emanating from the tissue 160 is then collected by the lens 122, which directs the signal beam 150 toward the photo-refractive crystal 128 for subsequent interference with the reference beam 145. For example, the photo-refractive crystal 128 may comprise a BSO crystal having a holographic cut along the [001], [110], and [110] directions, or any other suitable photo-refractive crystal.

As the signal beam 150 propagates through the photo-refractive crystal 128, it is amplified in the two-wave mixing process by a gain $\gamma$. To enhance the two-wave mixing gain $\gamma$, the signal source 142 in conjunction with the HV amplifier 144 may be employed to apply an AC field to the crystal 128. For example, the AC field may comprise a 4 kHz field of 10 kV/cm peak-to-peak high voltage, or any other suitable AC field. After the signal beam 150 passes through the crystal 128, the apertures 129 and 131 operate to prevent any light from the reference beam 145 scattered by the edges of the crystal 128 from reaching the photo-diode 134. Further, the two lenses 130 and 132 operate to collect the light from a signal beam 152 resulting from the two-wave mixing process, and to focus the signal beam 152 onto the photo-diode 134. The band-pass filter 133 is operative to eliminate substantially all ambient light from reaching the photo-diode 134.

Figure 2:
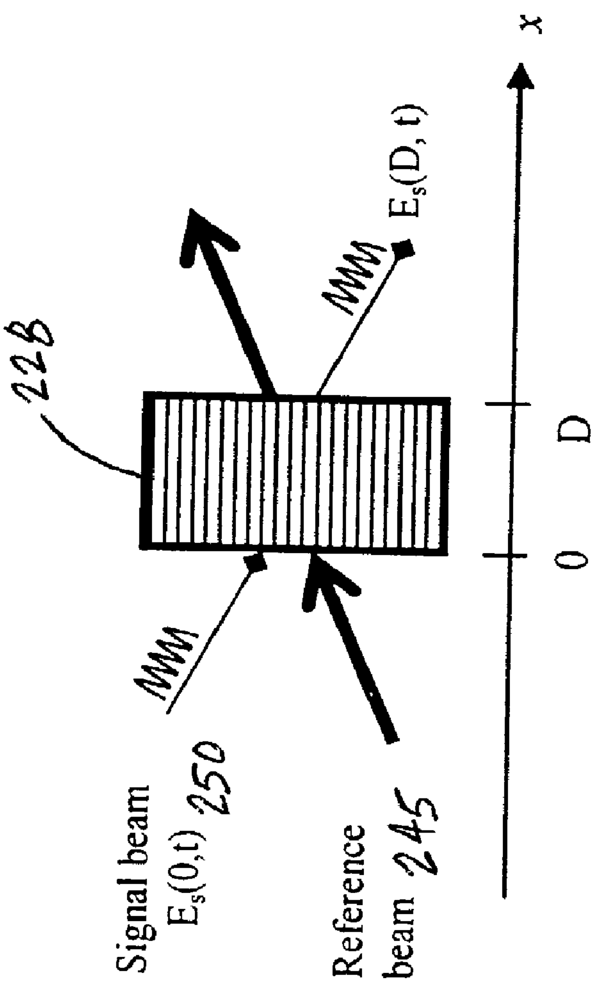
FIG. 2 is a diagram illustrating the operation of a photo-refractive crystal employed in the detection system of FIG. 1.

The operation of the photo-refractive crystal 128 for implementing the above-described two-wave mixing process will be better understood by reference to FIG. 2. As shown in FIG. 2, a reference beam 245 and a diffuse signal beam 250 are provided to a photo-refractive crystal 228. It is appreciated that the reference beam 245 corresponds to the reference beam 145 (see FIG. 1), and the diffuse signal beam 250 corresponds to the diffuse signal beam 150 (see FIG. 1). It is also understood that like the reference and signal beams 145 and 150, the reference and signal beams 245 and 250 are derived from the same optical signal source.

In the illustrated embodiment, the reference beam 245 and the signal beam 250 comprise respective plane waves that interfere with one another within the photo-refractive crystal 228, which has a predetermined thickness D. The signal beam 250 has an amplitude represented by $E_s(0,t)$ before entering the crystal 228, and an amplitude represented by $E_s(D,t)$ after exiting the crystal 228. It this analysis, it is assumed that the signal beam 250 has been phase-modulated by an acoustic field at a frequency high enough to assure that the response time of the crystal 228 is large relative to the oscillation period of the signal beam. It is further assumed that the index of refraction of the crystal 228 is modulated through the electro-optic effect, as known in the art, and the reference beam 245 is diffracted off of the index grating in the direction of the signal beam 250 in the two-wave mixing process. More specifically, the modulation of the index of refraction of the photo-refractive crystal 228 creates a hologram, and the reference beam 245 diffracts off of this hologram to provide an exact replica of the signal beam 250. A high voltage AC field externally applied to the crystal 228 enhances the reconstruction efficiency and therefore the detection sensitivity, as described in greater detail below.

As the signal beam 250 propagates through the photo-refractive crystal 228, it undergoes amplification proportional to the two-wave mixing gain γ as the reference beam 245 is diffracted into the path of the beam 250. For example, the diffracted reference beam 245 may be uniformly shifted in phase relative to the signal beam 250. It is noted that the reference beam 245 has substantially the same wave front as the signal beam 250, but does not acquire the high frequency phase modulation of the signal beam 250.

The gain coefficient γ is a complex value, i.e., $$\gamma=\gamma'+i\gamma'', \tag{1}$$

in which "γ'" is the real part of the two-wave mixing gain γ, and "γ"" is the imaginary part of the gain γ. Further, the photo-refractive crystal 228 has an optical absorption coefficient α. In the event the reference beam 245 has an intensity that is large relative to the intensity of the signal beam 250, the amplitude of the signal beam 250 exiting the crystal 228 may be expressed as $$E_s(D,t)=e^{\left(\frac{-\alpha D}{2}\right)}E_s(0,0)[(e^{\gamma D}-1)+e^{i\phi_\alpha \sin\omega_\alpha t}], \tag{2}$$

in which "$e^{\gamma D}-1$" represents the diffracted reference beam 245, "$e^{i\phi_\alpha \sin\,\omega_\alpha t}$" represents the diffuse signal beam 250, "$\phi_\alpha$" is the amplitude of the phase modulation, and "$\omega_\alpha$" is the angular frequency of the phase modulation. Accordingly, the intensity of the signal beam 250 exiting the crystal 228 may be expressed as $$I_s(D,t)=e^{-\alpha D}I_s(0,0)[|e^{\gamma D}-1|^2+1+2Re[(e^{\gamma D}-1)^*e^{i\phi_\alpha \sin\,\omega_\alpha t}]], \tag{3}$$

in which $$I_s(0,0)=|E_s(0,0)|^2, \tag{4}$$

and "*" denotes the complex conjugate.

It is appreciated that equation (3) may be expanded in terms of its DC and AC components, using Bessel functions and retaining the lowest order terms. Specifically, the DC component may be expressed as $$I_{DC}(D,t)=e^{(-\alpha D)}I_s(0,0)\{|e^{\lambda D}-1|^2+1+2[e^{\gamma' D}\cos(\gamma'' D)-1]J_0(\phi_\alpha)\}, \tag{5}$$

and the AC component may be expressed as $$I_{AC}(D,t)=4e^{-\alpha D}I_s(0,0)e^{\gamma' D}\sin(\gamma'' D)J_1(\phi_\alpha)\sin(\omega_\alpha t). \tag{6}$$

As indicated in equation (5), the DC component of the signal exhibits a zero-order Bessel function dependence on the amplitude of phase modulation. The amplitude of phase modulation scales with the acoustic pressure amplitude, and may or may not be time dependent depending on whether CW or pulsed ultrasound is employed. Further, as indicated in equation (6), the AC component is time dependent, and constitutes a first-order Bessel function.

Accordingly, after the signal beam 250 passes through the photo-refractive crystal 228, the signal beam intensity has a DC component, as expressed in equation (5), and an AC component, as expressed in equation (6). The DC component of equation (5) represents a DC signal that can be used as a measure of the magnitude of the mean phase shift induced by the ultrasound on the multiply scattered optical field within the turbid medium. It is noted that equations (5)-(6) are representative of a signal beam incident on the photo-refractive crystal 228 having a fixed, time-dependent phase modulation corresponding to a single optical path.

For acousto-photonic imaging in highly scattered media, light generally travels over multiple paths. Further, the AC component of the signal observed at a single detector generally comprises the summation of the AC signal components from each one of the paths. Because the phase modulation induced by the ultrasound is typically not spatially uniform, the AC components of the signals may not add coherently at the photo-detector, and therefore may not provide a good measurement of the magnitude of the mean phase shift. However, because the DC offset depends on the amplitude of the phase modulation, and because the DC offset is typically substantially larger than the AC component, the DC offset may be employed to provide a better measurement of the magnitude of the mean phase shift induced by the ultrasound on the multiply scattered optical field. In the preferred embodiment, to maximize the DC offset signal, the reference beam 245 is in-phase with the signal beam 250, resulting in a photo-refractive gain expressible as a pure, real value.

The presently disclosed system 100 for detecting acousto-photonic emissions in optically turbid media is further described below with reference to the following illustrative example. In this example, the sound source 101 included in the detection system 100 (see FIG. 1) is operative to produce a pulse train comprising 20 cycle pulses with a pulse repetition frequency (PRF) of 100 Hz. Further, a plurality of acousto-photonic imaging (API) signals is analyzed, having passed through the biological tissue sample 160 with a scattering coefficient $\mu_s$ equal to about 3 $cm^{-1}$.

Figure 3A:
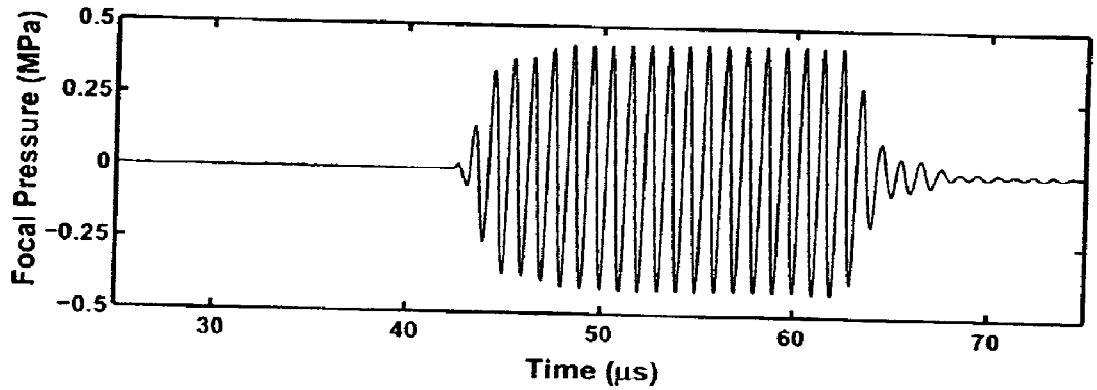
FIG. 3*a* is a diagram illustrating the measured focal pressure generated by a sound source included in the detection system of FIG. 1.
Figure 3B:
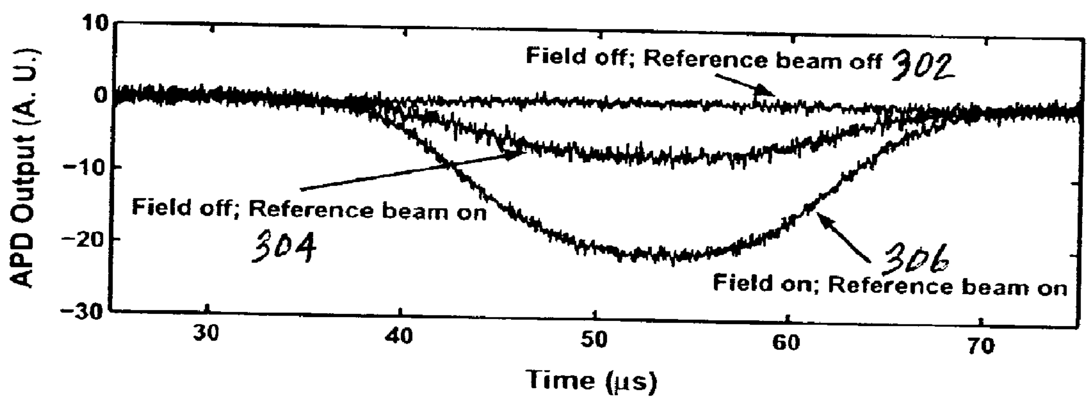
FIG. 3*b* is a diagram illustrating acousto-photonic emissions detected by the detection system of FIG. 1, including a first signal detected in the absence of a reference beam provided to the photo-refractive crystal (PRC), a second signal detected in the presence of the reference signal provided to the PRC, and a third signal detected in the presence of the reference signal and an AC field applied to the PRC.

FIG. 3*a* depicts a diagram of the measured focal pressure generated by the sound source 101 driven by a 20-cycle pulse at a 1 MHz center frequency. As shown in FIG. 3*a*, the peak measured focal pressure is about 0.4 MPa. FIG. 3*b* depicts a diagram of three resulting API signals 302, 304, and 306. Each one of the API signals 302, 304, and 306 corresponds to a representation of the signal beam 150 (see FIG. 1), which has passed through the biological tissue 160. For example, the API signals 302, 304, and 306 can be detected by the photodiode 134, amplified by the pre-amplifier 136, and displayed by the oscilloscope 138. It is also noted that data corresponding to the API signals 302, 304, and 306 may also be provided to the computer 140 for further analysis.

Specifically, the signal 302 represents an API signal detected by the photo-detector 127 in the absence of a reference beam (e.g., the reference beam 145) provided to the photo-refractive crystal 128, and in the absence of an AC field applied to the crystal 128. As shown in FIG. 3*b*, the API signal 302 exhibits essentially no DC offset. The signal 304 represents an API signal detected by the photo-detector 127 in the absence of an applied AC field, but in the presence of a reference beam provided to the photo-refractive crystal 128. Moreover, the signal 306 represents an API signal detected by the photo-detector 127 in the presence of both an applied AC field and a reference beam provided to the crystal 128. As described above, the AC field generated by the signal source 142 and the HV amplifier 144 typically operates to increase the two-wave mixing gain γ. Moreover, the mixing of the reference beam and the corresponding signal beams within the crystal 128 causes the resulting API signals 304 and 306 to track the envelope of the 20 cycle pulse train in the time domain (see also FIG. 3*a*). Accordingly, each one of the API signals 304 and 306 depicted in FIG. 3*b* has a DC offset, as expressed in equation (5).

As shown in FIG. 3*b*, the mixing of the signal beam and the reference beam induced by the photo-refractive crystal and facilitated by the applied AC field significantly enhances the DC offset of the API signals 304 and 306. It is noted that in this example, the diffracted reference beam is in-phase with the signal beam, causing the photo-refractive gain to be purely real. As a result, the 1 MHz modulation of the 20 cycle pulse train is typically not observable on the API signals 302, 304, and 306. It is further noted that even if the diffracted reference beam were in quadrature with the signal beam, the 1 MHz signal would typically be negligible relative to the DC offset of the API signals 304 and 306.

It should be appreciated that the API signal data illustrated in FIG. 3*b* corresponds to a simple coherent averaging of multiple waveforms. Such coherent averaging in the time domain permits the use of acoustic pulses instead of continuous-wave (CW) ultrasound in the detection system 100 of FIG. 1, thereby increasing the spatial resolution along the axis of the ultrasonic transducer 120 and reducing deleterious thermal bio-effects.

Figure 4:
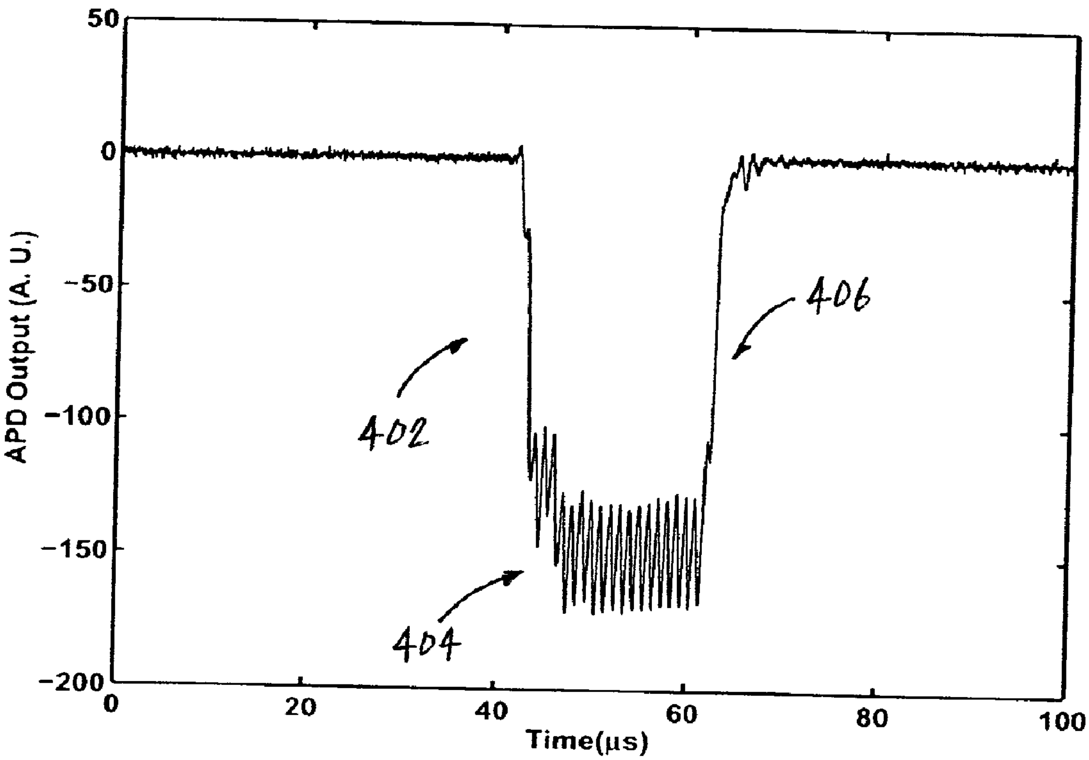
FIG. 4 is a diagram of a fourth signal detected by the detection system of FIG. 1, showing an AC component and a DC offset of the detected signal. The fourth detected signal of FIG. 4 corresponds to an acousto-photonic signal emitted from substantially transparent media.

FIG. 4 depicts another API signal 402 corresponding to the measured focal pressure of FIG. 3*a*. Like the API signals 302, 304, and 306 (see FIG. 3*b*), the API signal 402 is a representation of the signal beam 150 (see FIG. 1) after passing through the biological tissue sample 160. In this case, however, it is assumed that the tissue 160 is not a turbid medium, but is substantially transparent. As shown in FIG. 4, the API signal 402 has an AC component 404 at the 1 MHz ultrasonic frequency, and a DC offset 406 that tracks the envelope of the 20 cycle pulse train. The presence of the AC component 404 indicates that the photo-refractive gain is not purely real, but has a small imaginary component such that $I_{AC}(D,t)$, as expressed in equation (6), does not go to zero. The reduced levels of the AC component in the API signals 302, 304, and 306 (see FIG. 3*b*) are due to the increased levels of diffusivity in the tissue sample. It is noted that the AC component 404 of the API signal 402 is not spatially coherent over the wave front. For this reason, when the scattered light of the API signal 402 is collected using a single detector, the level of the AC component 404 is typically significantly reduced. However, the larger DC offset signal 406 survives, and, in accordance with equation (5), is directly related to the ultrasonically-induced phase shift. The DC offset signal 406 may therefore be used as a direct measure of the level of acousto-photonic interaction within the acoustic focal region of the tissue sample.

Because the DC offset of the API signals detected by the presently disclosed detection system 100 (see FIG. 1) can be integrated over large area detectors, sensitivity can be significantly increased relative to conventional single detector techniques. Further, because the DC offset signal emanates from a volume of tissue delineated by the acoustic focal volume, the resolution of acousto-photonic imaging as herein described is essentially the same as that of conventional ultrasound techniques. Moreover, the detection of the DC offset signals makes it possible to operate in the time domain using pulsed ultrasound. In addition, there is a net gain in spatial resolution along the axis of the ultrasonic transducer, and a reduced potential for deleterious thermal bio-effects.

Figure 5:
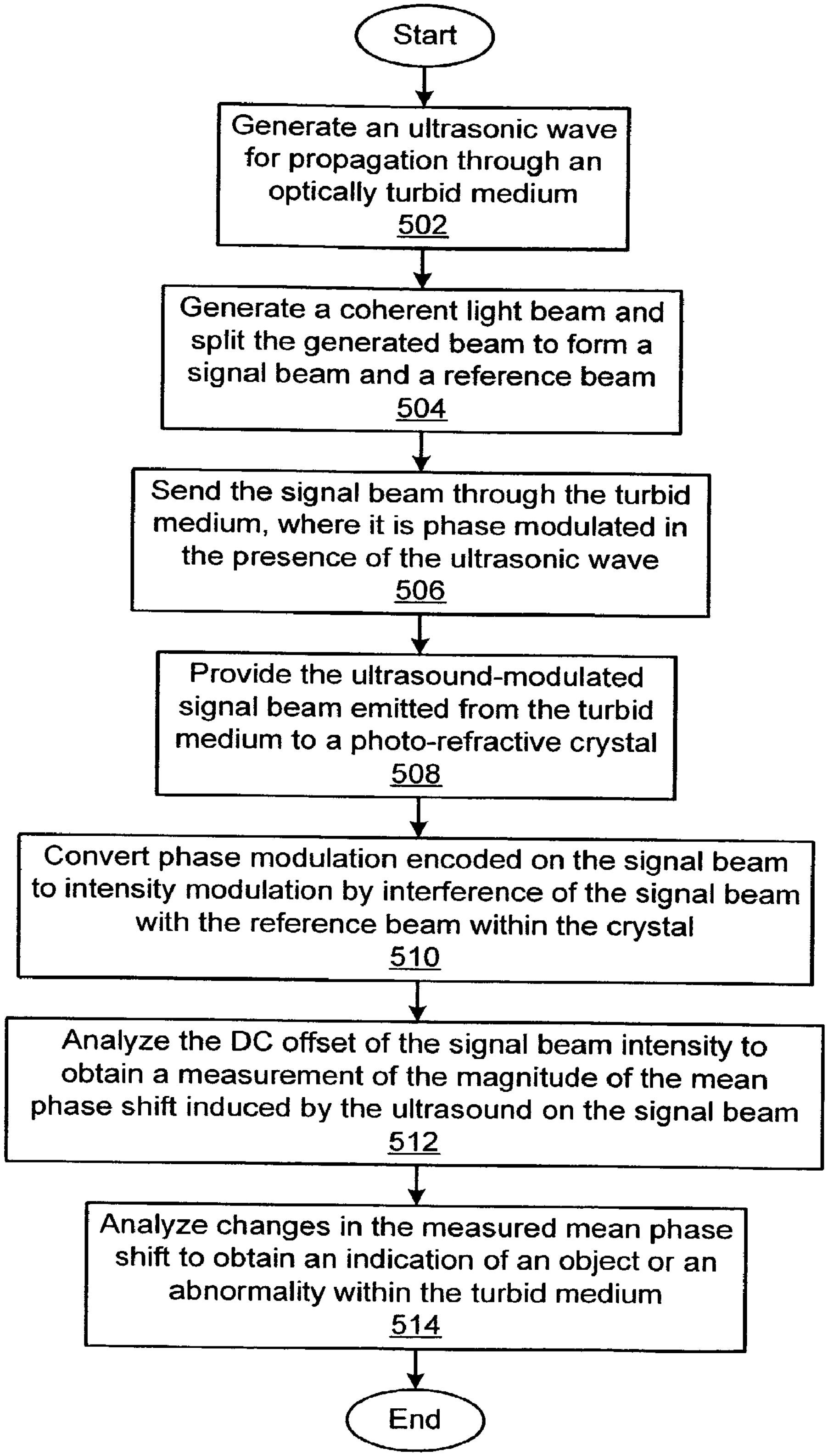
FIG. 5 is a flow diagram of a method of operating the detection system of FIG. 1.

A method of operating the presently disclosed system for detecting acousto-photonic emissions in optically turbid media is illustrated by reference to FIG. 5. As depicted in step 502, an ultrasonic wave is generated for subsequent propagation through an optically turbid medium such as a biological tissue. Next, a coherent beam of light is generated, as depicted in step 504, and subsequently split to form a signal beam and a reference beam. The signal beam is then sent, as depicted in step 506, through the turbid medium, where it is phase modulated in the presence of the ultrasonic wave. Next, an ultrasound-modulated signal beam is emitted, as depicted in step 508, from the turbid medium and provided to a photo-refractive crystal. The signal beam then interferes, as depicted in step 510, with the reference beam within the crystal to cause the phase modulation encoded on the signal beam to be converted to intensity modulation Next, a DC component of the signal beam intensity is analyzed, as depicted in step 512, to obtain a measurement of the magnitude of the mean phase shift induced by the ultrasound on the diffusely scattered signal beam within the turbid medium. Changes in the measured mean phase shift are then analyzed, as depicted in step 514, to obtain an indication of an object or an abnormality at the interaction region of the ultrasonic wave and the laser light within the turbid medium.

Although the preferred embodiment of the presently disclosed detection system and method has been described in terms of the detection of objects and abnormalities in biological tissue such as breast and brain tissue, it should be appreciated that the disclosed system and method may also be used to perform tissue characterization relating to optical descriptors (e.g., absorption and scattering) and/or mechanical descriptors (e.g., absorption and speed). It should further be appreciated that the disclosed system and method may be used to acquire images of different structures within other turbid media outside the medical field including underwater detection, atmosphere optics, and any other suitable field involving turbid media.

It will also be appreciated by those of ordinary skill in the art that further modifications to and variations of the above-described enhanced detection of acousto-photonic emissions in optically turbid media using a photo-refractive crystal-based detection system may be made without departing from the inventive concepts disclosed herein. Accordingly, the invention should not be viewed as limited except as by the scope and spirit of the appended claims.

What is claimed is:

1. A system for detecting acousto-photonic emissions in optically turbid media, comprising:

a sound source for generating an ultrasonic wave for propagation through an optically turbid medium;

a light source for generating a signal light beam for transmission through the optically turbid medium, and for generating a reference light beam, wherein the signal light beam is phase modulated in the presence of the ultrasonic wave within an interaction region of the optically turbid medium;

a photo-detector including a photo-refractive crystal for receiving the phase modulated signal light beam and the reference light beam, and for converting the phase modulated signal light beam to an intensity modulated signal light beam by interference of the phase modulated signal light beam and the reference light beam within the photo-refractive crystal, the intensity modulated signal light beam having a DC component; and a signal analyzer for analyzing the DC component of the intensity modulated signal light beam to obtain a measure of a magnitude of a mean phase shift induced by the ultrasonic wave on the signal light beam within the interaction region of the optically turbid medium, and for analyzing at least one change in the magnitude of the mean phase shift, the at least one change in the magnitude of the mean phase shift being indicative of an object or an abnormality at the interaction region of the optically turbid medium.

2. The system of claim 1 wherein the sound source includes an acoustic transducer.

3. The system of claim 2 wherein the acoustic transducer comprises a piezoelectric transducer.

4. The system of claim 1:

wherein the light source includes a laser for generating a coherent light beam, and a beam splitter for splitting the coherent light beam to produce the signal light beam and the reference light beam.

5. The system of claim 1 wherein the photo-detector further includes a photo-diode for receiving the intensity modulated signal light beam.

6. The system of claim 1 further including an AC field source for providing an AC field to the photo-refractive crystal.

7. A method of detecting acousto-photonic emissions in optically turbid media, comprising the steps of:

generating, by a sound source, an ultrasonic wave for propagation through an optically turbid medium;

generating, by a light source, a signal light beam and a reference light beam, the signal light beam for transmission through the optically turbid medium, wherein the signal light beam is phase modulated in the presence of the ultrasonic wave within an interaction region of the optically turbid medium;

converting the phase modulated signal light beam to an intensity modulated signal light beam by interference of the phase modulated signal light beam and the reference light beam within a photo-refractive crystal, the intensity modulated signal light beam having a DC component;

analyzing, by a signal analyzer, the DC component of the intensity modulated signal light beam to obtain a measure of a magnitude of a mean phase shift induced by the ultrasonic wave on the signal light beam within the interaction region of the optically turbid medium; and analyzing, by the signal analyzer, at least one change in the magnitude of the mean phase shift induced by the ultrasonic wave on the signal light beam, the at least one change in the magnitude of the mean phase shift being indicative of an object or an abnormality at the interaction region of the optically turbid medium.

8. The method of claim 7:

wherein the sound source includes an acoustic transducer; and wherein the generating of the ultrasonic wave includes generating the ultrasonic wave using the acoustic transducer.

9. The method of claim 8:

wherein the acoustic transducer comprises a piezoelectric transducer; and wherein the generating of the ultrasonic wave includes generating the ultrasonic wave using the piezoelectric transducer.

10. The method of claim 7:

wherein the light source includes a laser; and wherein the generating of the signal light beam and the reference light beam includes generating the signal light beam and the reference light beam using the laser.

11. The method of claim 10 wherein the generating of the signal light beam further includes:

generating, by the laser, a coherent light beam; and splitting the coherent light beam to produce the signal light beam and the reference light beam.

12. The method of claim 7 further including providing an AC field to the photo-refractive crystal.

* * * * *

UNITED STATES PATENT AND TRADEMARK OFFICE

CERTIFICATE OF CORRECTION

PATENT NO. : 7,652,773 B2
APPLICATION NO. : 10/586713
DATED : January 26, 2010
INVENTOR(S) : Charles A. DiMarzio et al.

It is certified that error appears in the above-identified patent and that said Letters Patent is hereby corrected as shown below:

Column 6, line 45, “and [110]” should read -- and $[1\bar{1}0]$; --; and

Column 10, line 33, “modulation Next,” should read --modulation. Next,--.

Signed and Sealed this

Twelfth Day of October, 2010

David J. Kappos

*Director of the United States Patent and Trademark Office*